(12) United States Patent
Schleicher (10) Patent No.: US 7,367,874 B2
(45) Date of Patent: May 6, 2008

(54) MANDREL FOR WORKING DISKS

(75) Inventor: Wolfgang Schleicher, Riedenburg (DE)

(73) Assignee: DFS-Diamon GmbH, Riedenburg (DE)

( * ) Notice: Subject to any disclaimer, the term of this patent is extended or adjusted under 35 U.S.C. 154(b) by 72 days.

(21) Appl. No.: 11/214,586

(22) Filed: Aug. 30, 2005

(65) Prior Publication Data

US 2005/0287936 A1  Dec. 29, 2005

Related U.S. Application Data (63) Continuation of application No. PCT/DE2004/000371, filed on Feb. 27, 2004.

(30) Foreign Application Priority Data

| Mar. 6, 2003 | (DE) | 203 03 657 U |
| Apr. 16, 2003 | (DE) | 203 06 147 U |
| Jul. 28, 2003 | (DE) | 203 11 608 U |

(51) Int. Cl.
*B24B 23/00* (2006.01)

(52) U.S. Cl. .............. 451/342; 451/508; 451/911

(58) Field of Classification Search ............. 451/911, 451/342, 541, 509, 508
See application file for complete search history.

(56) References Cited

U.S. PATENT DOCUMENTS

| 302,952 | A | * | 8/1884 | Smith | 451/548 |
| 428,019 | A | * | 5/1890 | Pugh | 433/135 |
| 881,691 | A | | 3/1908 | Hughes | |
| 1,130,914 | A | * | 3/1915 | Maker | 433/134 |
| 1,417,584 | A | * | 5/1922 | Stempel, Jr. | 433/135 |
| 1,443,079 | A | * | 1/1923 | Lefebvre et al. | 433/134 |
| 1,941,830 | A | * | 1/1934 | Dunn | 160/176.1 R |
| 1,987,830 | A | * | 1/1935 | Kelsey | 433/134 |
| 2,426,170 | A | | 8/1947 | Akers | |
| 4,889,489 | A | | 12/1989 | Von Weissenfluh | |

FOREIGN PATENT DOCUMENTS

| DE | 33 05 644 A1 | 8/1984 |
| DE | 197 48 038 A1 | 5/1999 |
| DE | 100 39 446 A1 | 2/2002 |
| EP | 0 147 545 A1 | 7/1985 |
| EP | 0 832 614 A1 | 4/1998 |
| WO | WO 88/00029 | 1/1988 |

* cited by examiner

*Primary Examiner*—Robert Rose
(74) *Attorney, Agent, or Firm*—Laurence A. Greenberg; Werner H. Stemer; Ralph E. Locher (57) ABSTRACT

A mandrel or a clamping element for working disks, for example, separating disks, grinding disks and/or polishing disks, contains a shaft to fix the mandrel to a receiving element or to a clamping element of a working machine. The mandrel has a fixing element for detachable fixing and clamping the working disk between a clamping surface formed on one end of the mandrel and the fixing element. A working disk, which can be used on a mandrel or on a clamping element, contains a fixing opening, having a cross-section that deviates from that of a circle, on a receiving element of the mandrel reaching through the opening in a form-fitting manner.

12 Claims, 6 Drawing Sheets

MANDREL FOR WORKING DISKS

CROSS-REFERENCE TO RELATED APPLICATION

This is a continuing application, under 35 U.S.C. § 120, of copending international application No. PCT/DE2004/000371, filed Feb. 27, 2004, which designated the United States; this application also claims the priority, under 35 U.S.C. § 119, of German patent application No. 203 03 657.3, filed Mar. 6, 2003, No. 203 06 147.0, filed Apr. 16, 2003, and No. 203 11 608.9, filed Jul. 28, 2003; the prior applications are herewith incorporated by reference in their entirety.

BACKGROUND OF THE INVENTION

FIELD OF THE INVENTION

The invention relates to a mandrel or clamping element for working disks, i.e. in particular for cut-off disks, diamond disks and/or polishing disks. The mandrel has a shaft for affixing the mandrel to a retainer or clamping device of an instrument and a fixing element for affixing and clamping the working disk in a detachable manner between a clamping surface formed at one end of the mandrel and the fixing element.

The invention furthermore relates to a working disk for use on a mandrel or clamping element, such as a cut-off disk, a diamond disk and/or a polishing disk. The working disk has at least one attachment opening in the center of the disk, which is penetrated by the mandrel when the working disk is affixed to the mandrel.

Furthermore, the invention relates to a working disk-mandrel combination. The working disk-mandrel combination contains one mandrel and one working disk, such as a cut-off, grinding or polishing disk.

Working disks, including those in particular which are used in dental technology, are available in a wide range of configurations, including cut-off disks, diamond disks and polishing disks. In order to be able to affix working disks of this type to a retainer driven by rotation, such as a clamping chuck of a machine, it is necessary to first affix the working disk currently being used to a mandrel or clamping element, which essentially is formed of a shaft which can be connected with the machine retainer or the clamping chuck of the machine and of mechanisms for detachably affixing the working disk to one end of this shaft, or to a head piece located there. These mechanisms for detachably affixing the working disks are usually tensioning nuts or tensioning screws. It therefore takes a relatively long time to affix or release a working disk to or from a mandrel, i.e. approximately two minutes are usually required to complete this procedure.

SUMMARY OF THE INVENTION

It is accordingly an object of the invention to provide a mandrel for working disks which overcomes the above-mentioned disadvantages of the prior art devices of this general type, which makes it possible to affix and release a working disk in a simple, fast manner. The object of the invention is furthermore to provide a working disk that makes simple, fast affixing and releasing to or from a mandrel possible.

With the foregoing and other objects in view there is provided, in accordance with the invention, a mandrel functioning as a clamping element for a working disk. The mandrel contains a shaft for affixing the mandrel to a retainer or clamping device of an instrument. The shaft has an end with a clamping surface and an opening formed therein. A detachable fixing element is provided for affixing and clamping the working disk in a detachable manner between the clamping surface and the detachable fixing element. The detachable fixing element is a pin with a pin shaft and a pin head extending from the pin shaft. The pin shaft is disposed in the opening. A mechanism is provided for anchoring the pin or the pin shaft of the pin in a detachable manner, and the mechanism is disposed in the opening.

The mandrel according to the invention is preferably developed in such a way as to enable the working disk to be affixed to the mandrel by a locking pin, which creates a pin, and which forms a head piece at the end of the shaft, and which can be inserted with its shaft into an opening of the mandrel. The axis of which is the same as the longitudinal axis of the mandrel, and which can be locked into place there, so that the working disk is retained between the head piece of the pin and a bearing surface of the mandrel, while at the same time sitting on the retainer of the mandrel in such a manner that prevents it from rotating.

The working disk according to the invention is particularly suitable for use with a mandrel which contains a retainer in order to affix the working disk in a manner which prevents it from rotating, which has a profile that deviates from that of the circular form, and to which the working disk, with its attachment opening which also contains the profile which deviates from the circular form, can be affixed by pushing it in or placing it on with a positive fit.

In accordance with an added feature of the invention, the mechanism is a latching mechanism for detachably anchoring of the pin or the pin shaft and/or a bayonet lock.

In accordance with another feature of the invention, the mandrel has a longitudinal axis and the opening is formed parallel to the longitudinal axis. Ideally, the end of the shaft is a headpiece.

In accordance with an additional feature of the invention, the latching mechanism includes at least one elastic latching element produced from a same material as the shaft or the headpiece, and the pin shaft has at least one recess for engaging the elastic latching element. The elastic latching element is one of at least two elastic latching elements fitted at an offset around the longitudinal axis of the mandrel, and the recess on the pin shaft forms a counter-latching element assigned to each of the elastic latching element.

In accordance with a further feature of the invention, on a circumference of the pin shaft, in a direction of the circumference, the recess is formed and alternates with at least one area of the circumference of the pin shaft where the pin shaft does not have the recess and thus forms the counter-latching element.

In accordance with another added feature of the invention, a retainer is disposed on the clamping surface, the retainer attaches the working disk and prevents the working disk from rotating.

In accordance with another embodiment of the invention, the mechanism is a protrusion extending into the opening, and the pin shaft has a groove. The groove is open at one end for receiving the protrusion formed in the opening.

In accordance with a further embodiment of the invention, the pin has a recess defining a tappet with a flattened surface running from one end of the pin for inserting the protrusion into the groove, and the tappet forms an angular surface on one side for the protrusion. Ideally, the pin has an axis, and in relation to the axis of the pin, the groove is formed as a partial length of a spiral or helicoidal line which encompasses the axis of the pin.

In accordance with a further embodiment of the invention, the clamping surface is formed on the headpiece and the fixing pin has a further clamping surface for engaging the working disk.

In accordance with an additional embodiment of the invention, at least one ring is fixed on the detachable fixing element or the shaft, the ring has an elastic working surface formed from a permanently elastic material. Preferably, the ring is an O-ring.

With the foregoing and other objects in view there is further provided, in accordance with the invention, a working disk for use on a mandrel functioning as a clamping element. The working disk contains a disk body having at least one attachment opening in a center of the disk body. The attachment opening is provided for being penetrated by the mandrel when the working disk is affixed to the mandrel. The attachment opening has a profile deviating from a circular form, and is shaped for a retainer of the mandrel which penetrates the opening with a form-locking fit.

In accordance with an added feature of the invention, the working disk is a cut-off disk, a diamond disk, and/or a polishing disk. The profile has a shape such as a square, a rectangle, or an oval.

In accordance with another feature of the invention, the profile of the attachment opening is defined by two straight, parallel edge lines and by further curved edge lines which link with the two first edge lines to form a closed edge.

In accordance with another further embodiment of the invention, a ring-type element is disposed on at least one side of the disk body, the ring-type element encompasses the attachment opening and is made of rubber elastic material.

In accordance with a concomitant feature of the invention, a ring-type element is disposed on at least one side of the disk body, the ring-type element has a ring-type section encompassing the attachment opening and is made of rubber elastic material.

Other features which are considered as characteristic for the invention are set forth in the appended claims.

Although the invention is illustrated and described herein as embodied in a mandrel for working disks, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
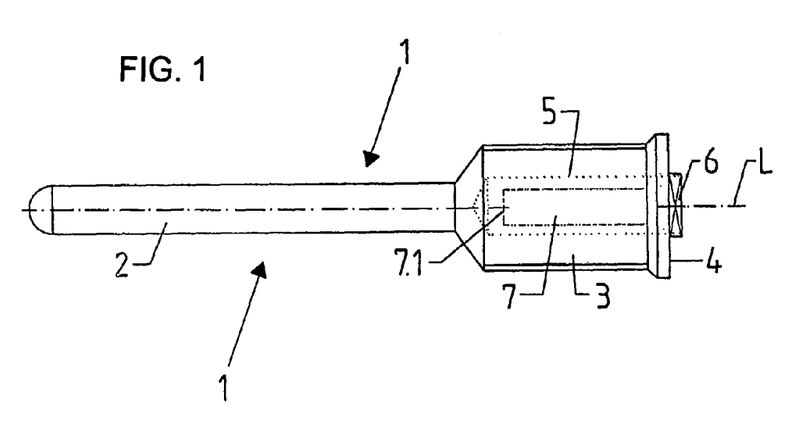
FIG. 1 is a diagrammatic, side-elevational view of a mandrel (click mandrel) for use with a working disk according to the invention.

Referring now to the figures of the drawing in detail and first, particularly, to FIG. 1 thereof, there is shown a mandrel 1 used for clamping working disks, such as cut-off, diamond and/or polishing disks, etc., for their use in an instrument not shown, such as a motor-driven clamping chuck.

The mandrel 1 is a single piece made of metal, for example, or another suitable material, and has a shaft 2 and a headpiece 3, which is fitted to the end of the shaft, and which like the shaft 2, is created with symmetrical rotation to a longitudinal axis L of the mandrel. The shaft 2 and the headpiece 3 are disposed together along the same axis.

In the headpiece 3, an opening 5 which is open and which is on the same axis as the longitudinal axis L has been fitted to a front side 4 which faces away from the shaft 2. Furthermore, a retainer 6 is formed which encompasses an edge of the opening 5, which enables each working disk to be affixed in a manner that prevents it from rotating. The retainer 6 is formed from a protrusion that has an outer diameter that deviates from the circular form, and which is adapted to the opening of a working disk.

On the headpiece 3, two compound spring-type spring sections 7 are formed, which are a single piece with the headpiece, and which are produced by slotting or lasering from the material of the headpiece 3, for example. The spring sections 7, which run in the direction of the longitudinal axis L, are connected on the end adjacent to their front surface 4 with the remainder of the head piece 3, and protrude together with their other spring section end 7.1, which is located away from the front surface 4, into the recess or opening 5.

Figure 3:
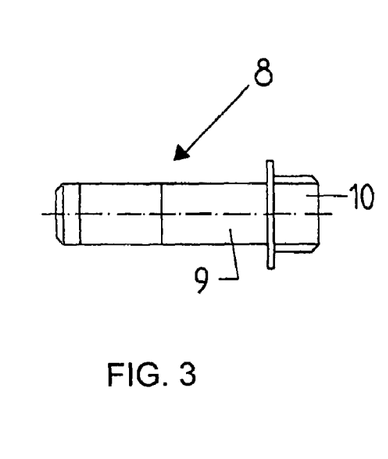
FIG. 3 is a diagrammatic, side-elevational view of a first embodiment of a click pin of the mandrel shown in FIGS. 1 and 2.
Figure 4:
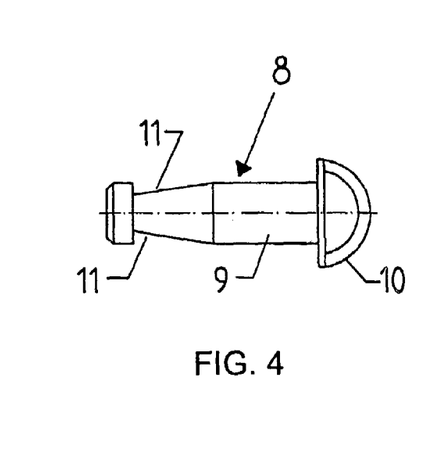
FIG. 4 is a diagrammatic, side-elevational view of a second embodiment of the click pin.
Figure 5:
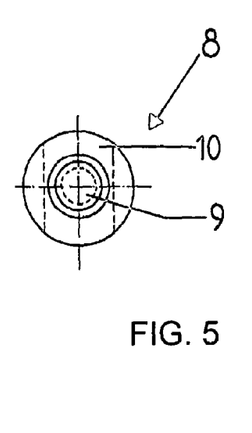
FIG. 5 is a diagrammatic, front-elevational view of a lower end of the pin.

In order to affix the cut-off disk currently being used to the headpiece 3, a click pin 8 is used, which has a shaft 9 with a head 10. At its end located away from the head 10, the shaft 9 is fitted with two recesses 11, which are also fitted, as are the two compound spring-type spring sections 7, at an offset of 180° around the longitudinal axis L. When the shaft 9 is pushed into the opening 5, the working disk currently being used can be secured onto the headpiece 3 between the front surface 4 located there and a head 10, any differences in the thickness of the disks being compensated for by elastic spacer disks. After the shaft 9 has been inserted into the recess 5, each compound spring-type spring section 7 locks with its end 7.1 into a recess 11, so that the click pin 8 is secured in the mandrel 1.

When the click pin 8 is turned by 90°, it can be unlatched, and as a result, the working disk currently being used can be removed from the click mandrel 1. During this turning motion, the end 7.1 of each spring section 7 slides radially outwards from the recess 11 onto the section of the shaft 9 which does not incorporate the recess, so that this can then be pulled out of the opening 5.

It is possible to clamp and remove the working disk currently being used to or from the mandrel 1 within a few seconds, while to date, the clamping procedure has taken a relatively long time to complete.

Figure 6:
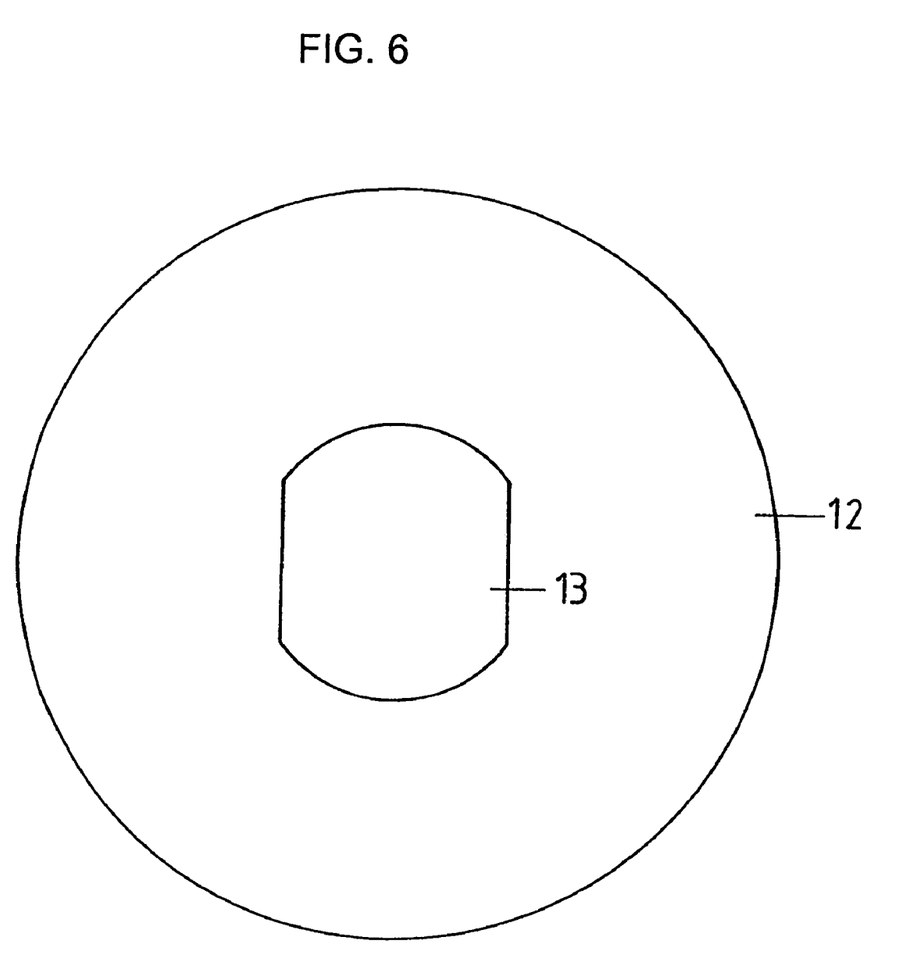
FIG. 6 is a diagrammatic, top plan view of a working disk according to the invention.

In FIG. 6, the working disk is labeled 12. The disk 12 has an attachment opening 13 in its center that deviates from the circular form, and with which the working disk 12 can be placed onto the retainer 6, which is formed from the protrusion that stands out over the front surface 4. The profile dimensions and profile form of the opening 13 and the retainer 6 are identical, so that after it is placed on, the retainer 6 is retained in the opening 13 with a form fit. A form fit being a fit that is dependent on the shape of the objects for interconnecting with each other.

Figure 7:
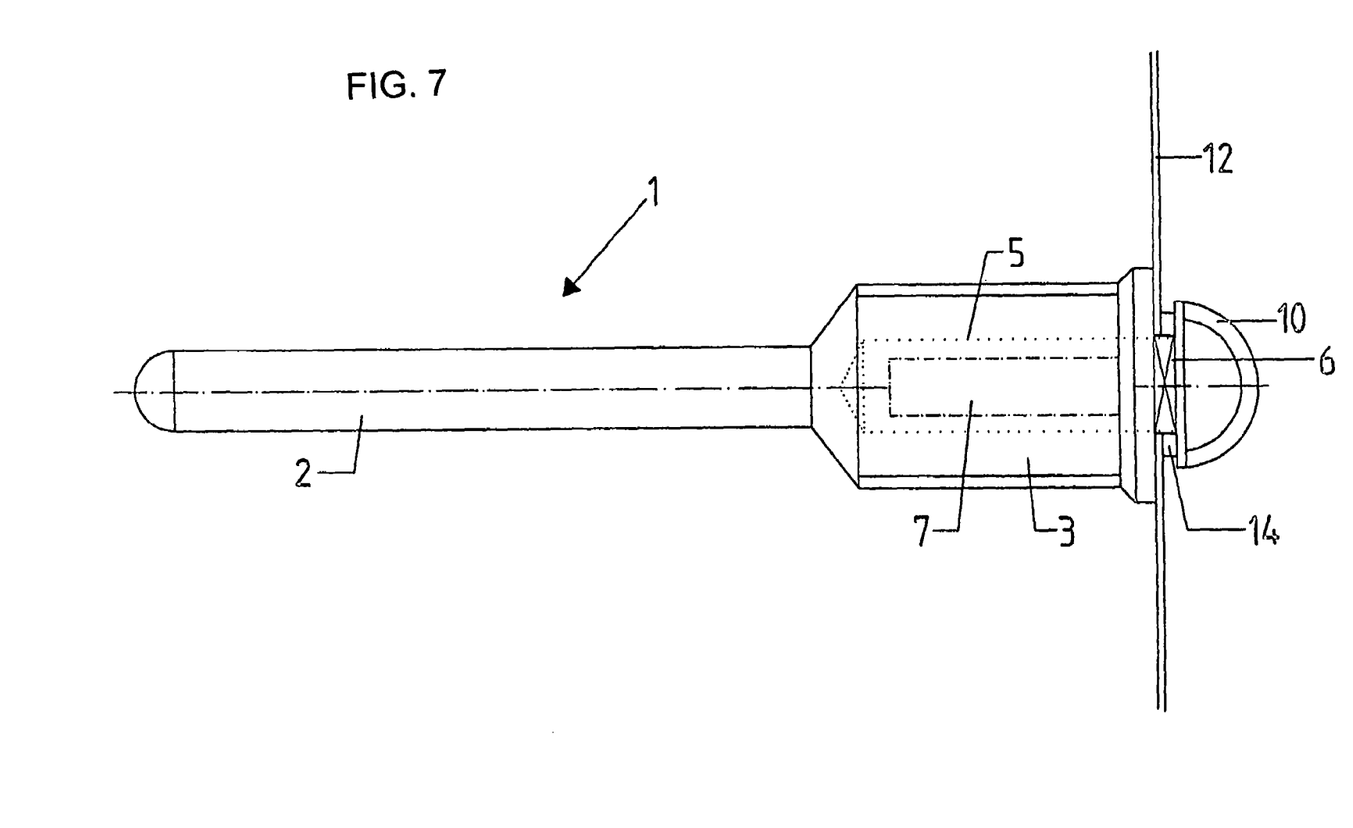
FIG. 7 is a diagrammatic, side-elevational view of the working disk and the mandrel.

FIG. 7 shows a simplified view of the working disk 12 which is affixed to the mandrel 1 and which sits on the retainer 6. This is clamped between the front surface 4 and an additional disk or a ring 14, which is formed of a rubber-elastic material, and which rests against the head 10. In the simplest scenario, the ring 14 is an O-ring, for example.

Instead of, or in addition to, the disk or the ring 14, it is also possible to make the head 10 permanently elastic on its side facing the shaft 9, for example by applying a suitable coating or by fitting the disk or the ring 14 firmly to the pin 8 or its head 10.

Furthermore, it is possible to fit the working disk currently being used 12 to at least one side in the area of the opening 13 with a ring-type, permanently elastic element or coat which encompasses this opening, for example with a ring or a disk made of a permanently elastic material.

Figure 8:
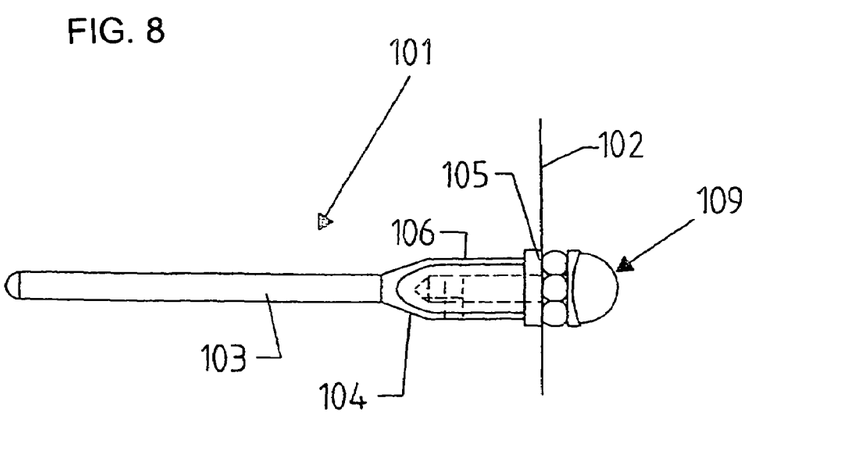
FIG. 8 is a diagrammatic, side-elevational view of a further embodiment of the mandrel according to the invention, together with a working or cut-off disk which has been clamped into place.
Figure 9:
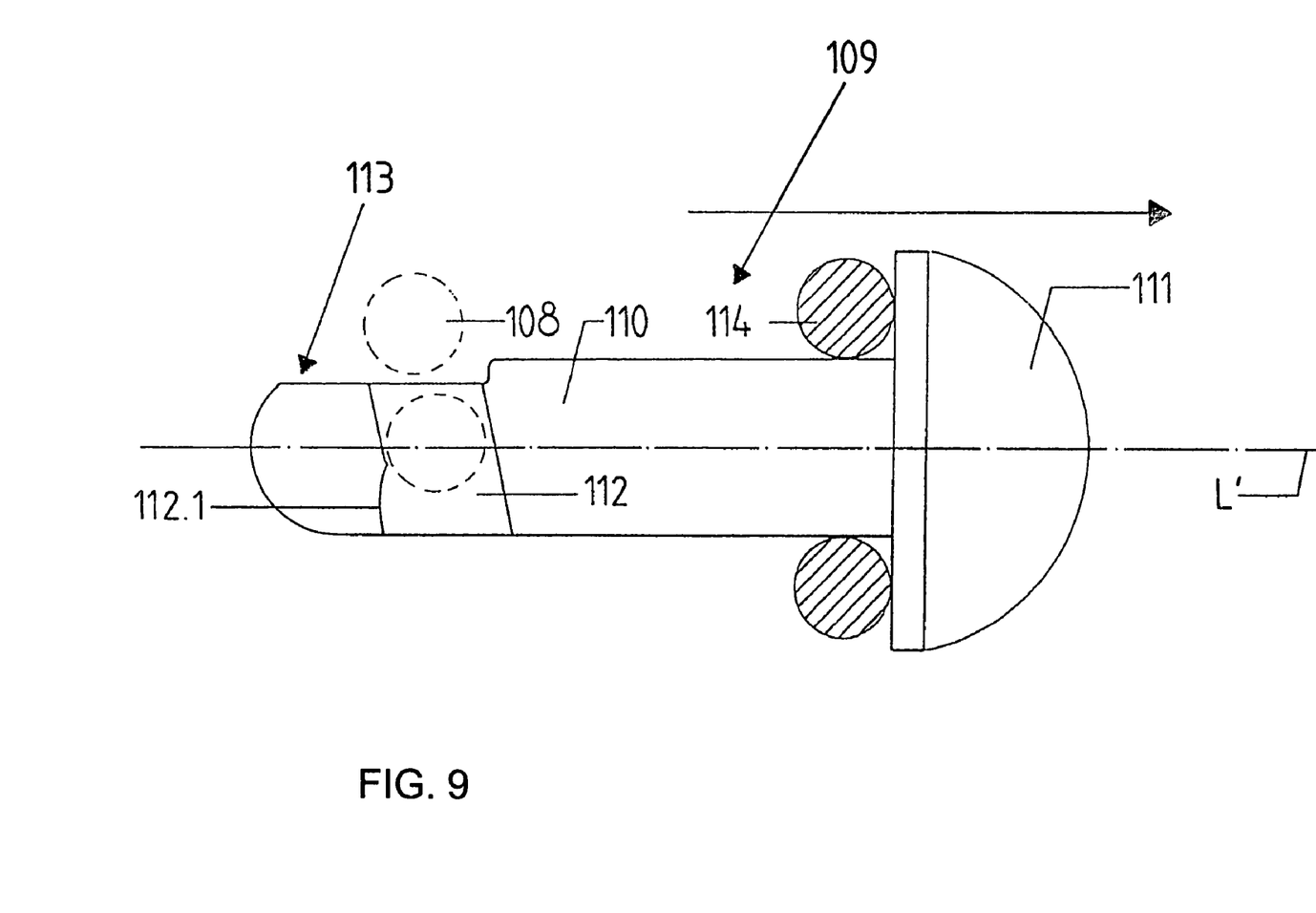
FIG. 9 is a diagrammatic, side-elevational view of a fixing pin and a head piece of the mandrel from FIG. 8.
Figure 10:
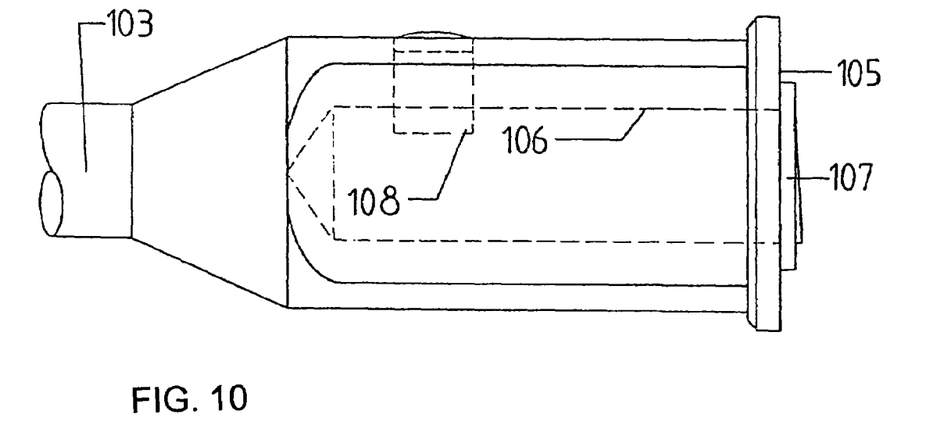
FIG. 10 is a diagrammatic, side-elevational view of the fixing pin and the head piece of the mandrel from FIG. 8.

The mandrel labeled overall as 101 in FIGS. 8-10 is used for clamping working disks 102, for example for clamping cut-off disks 102 or other working disks such as diamond and/or polishing disks etc. for use on an instrument not shown, such as a motor-driven clamping chuck not shown.

The mandrel 101 has a shaft 103 for clamping in the instrument, and a headpiece 104 which is created as a single piece with the shaft 103, which is fitted to one end of the shaft, and which, like the shaft 103, is created with symmetrical rotation to the longitudinal axis L of the mandrel. The shaft 103 and the headpiece 104 are furthermore disposed together along the same axis.

In the headpiece 104, an opening or drill hole 106 which is open and which is on the same axis as the longitudinal axis L has been fitted to the front side 105 which faces away from the shaft 103. Furthermore, a retainer 107 is formed which encompasses the edge of the opening 106, which enables each working disk 102 to be affixed in a manner that prevents it from rotating. The retainer 107 is formed from a protrusion that has an outer diameter which deviates from the circular form, and which is adapted to an opening of the working disk 102. Furthermore, a protrusion 108 that radially protrudes into the opening 106, is fitted to the headpiece 104, which in the embodiment of the invention shown is formed from a tappet which is inserted into the headpiece or into a drill hole located there and which is anchored in an appropriate manner.

In order to affix the working disk 102 to the headpiece 104, a fixing pin 109 is used, which has a shaft 110 with a head 111 that stands out radially over the outer surface of the shaft at one end of the shaft. At its end located away from the head 111, the shaft 110 is formed on its circumference with a groove 112 which is open in the direction facing the circumference, which runs in a convoluted or spiral manner towards the axis of the shaft 110, and which covers an area of the circumference which is less than 360° around the shaft 110, for example over an angle range of approximately 180°. Starting at its free end, the shaft 110 is fitted with a flattened surface 113 on one section of its circumference, or with a corresponding recess, into which the floor of the groove 112 merges at the end of the groove. The width of the groove 112 and the radial distance between the floor of the groove and the longitudinal axis L' of the fixing pin 109 and the depth of the flattened surface 113 are selected in such a way that when the shaft 110 is inserted into the opening 106 which has been adapted to the diameter of the shaft, the protrusion 108 first finds space in the flattened surface 113; then, when the fixing pin 109 is turned around its axis L', which then lies along the same axis as the axis L, the protrusion 108 enters the open end of the groove 112, whereby with continued turning, the head 111 of the fixing pin is moved along the axis towards the front surface 105 of the head piece 104 due to the convoluted path of the groove 112.

A ring 114 made of permanently elastic material, such as an O-ring, is disposed on the shaft 110, and rests against the side of the head 111 that faces towards the shaft 110. The working disk 102 currently being used is then pressed over this ring 114 against the front surface 105 by the fixing pin 109 which is affixed on the head piece 104, i.e. the working disk 102 which is sitting on the retainer 107 is then clamped between the front surface 105 and the ring 114. The working disk 102 is affixed in a particularly simple manner by inserting the shaft 110 into the opening 106 and by subsequently turning the fixing pin 109 by a slight angle, for example by an angle of 90° or slightly over 90°.

When the fixing pin 109 is turned back accordingly, and when this pin is removed from the opening 106, it is possible to remove the working disk 102 equally quickly.

Figure 2:
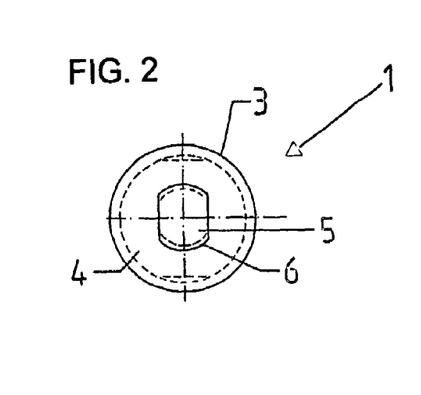
FIG. 2 is a diagrammatic, front-elevational view of the mandrel (click mandrel)

In general, the option is available of forming the groove 112 in such a way that the protrusion 108 elastically latches onto the groove 112 when locked, for which purpose the groove 112 is fitted with a recess or extension at the side, labeled with 112.1 in FIG. 2.

Figure 11:
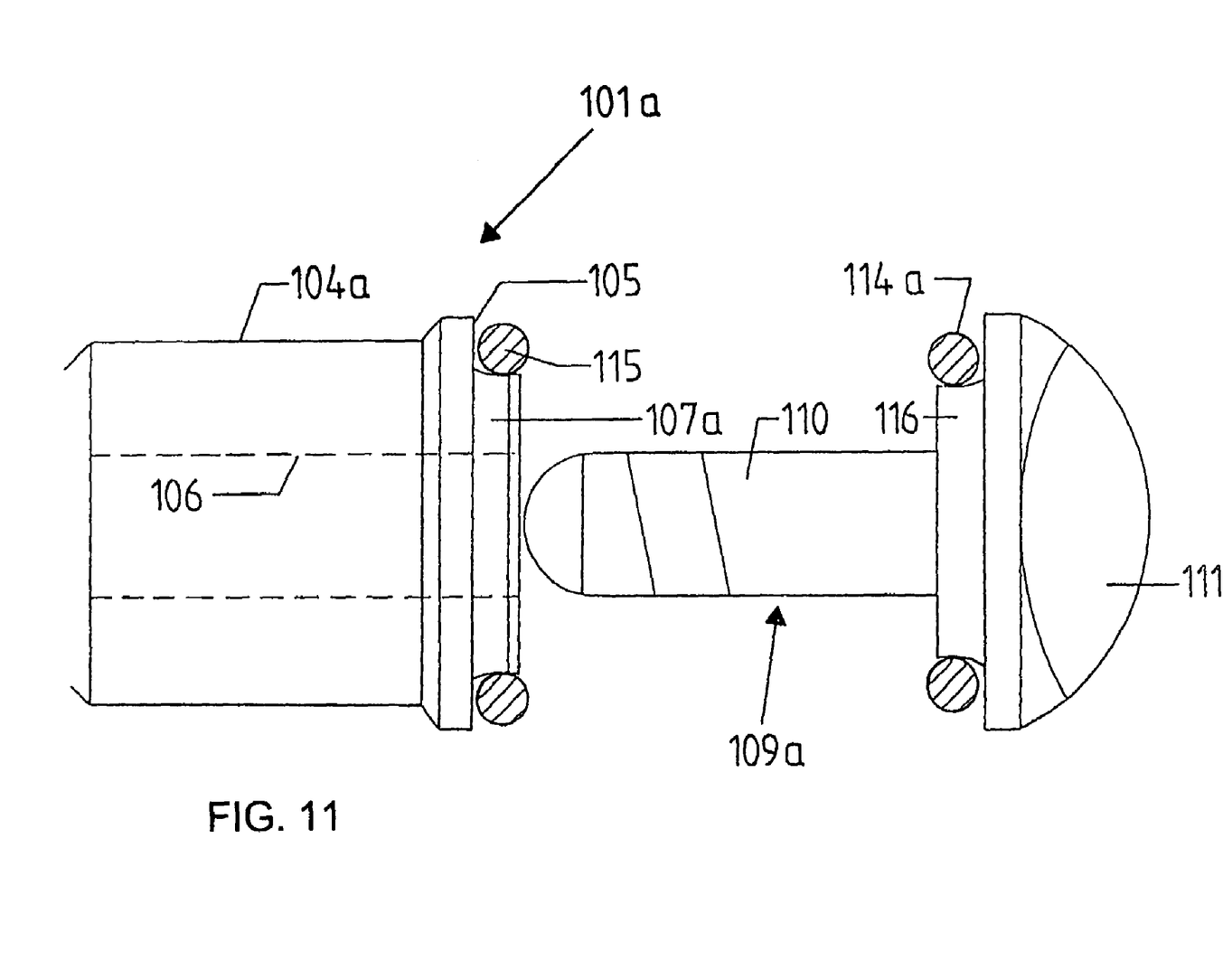
FIG. 11 is a diagrammatic, side-elevational view of the head piece and the fixing pin of the mandrel in a further possible embodiment of the invention.

FIG. 11 shows as a further possible embodiment of the invention a mandrel 101*a* to which a further elastic ring 115 is fitted to the headpiece 104*a* or to a protrusion 7*a* located there. The ring 115, together with the ring 114*a* which corresponds to the ring 114, has a significantly larger diameter than the diameter of the shaft 110. As with the ring 115, the ring 114*a* is also fitted to a protrusion 116, which is formed on the fixing pin 109*a* at the junction between the shaft 110 and the head 111. With this embodiment of the invention, the working disk currently being used is clamped over a relatively large diameter between the two rings 114*a* and 115. The mandrel 101*a* is therefore particularly suitable for use with thin working disks, in particular also with those with a relatively large diameter.

I claim:

1. A mandrel functioning as a clamping element for a working disk, the mandrel comprising:
   a shaft for affixing the mandrel to a retainer or clamping device of an instrument, said shaft having an end with a clamping surface and an opening formed therein;
   a detachable fixing element for affixing and clamping the working disk in a detachable manner between said clamping surface and said detachable fixing element, said detachable fixing element being a pin with a pin shaft and a pin head extending from said pin shaft, said pin shaft being disposable in said opening;

a mechanism for anchoring said pin or said pin shaft of said pin in said opening in a detachable manner; and a retainer disposed on said clamping surface, said retainer attaching the working disk for preventing the working disk from rotating;

said pin having a further clamping surface for engaging the working disk;

said clamping surface of said shaft or said further clamping surface of said pin being formed by at least one element made from a permanently elastic material;

said mechanism being a protrusion extending into said opening;

said pin shaft having a groove formed therein, said groove being open at one end for receiving said protrusion formed in said opening;

said pin having a recess formed therein defining a tappet with a flattened surface running from one end of said pin for inserting said protrusion into said groove; and said tappet forming an angular surface on one side for said protrusion.

2. The mandrel according to claim 1, wherein said mechanism is selected from the group consisting of a latching mechanism for detachably anchoring of said pin or the pin shaft and a bayonet lock.

3. The mandrel according to claim 2, wherein:

said mandrel has a longitudinal axis and said opening is formed parallel to said longitudinal axis; and said end of said shaft is a headpiece.

4. The mandrel according to claim 3, wherein:

said latching mechanism includes at least one elastic latching element produced from a same material as said shaft or said headpiece; and said pin shaft has at least one recess formed therein for engaging said elastic latching element.

5. A mandrel functioning as a clamping element for a working disk, the mandrel comprising:

a shaft for affixing the mandrel to a retainer or clamping device of an instrument, said shaft having an end with a clamping surface and an opening formed therein;

a detachable fixing element for affixing and clamping the working disk in a detachable manner between said clamping surface and said detachable fixing element, said detachable fixing element being a pin with a pin shaft and a pin head extending from said pin shaft, said pin shaft being disposable in said opening;

a mechanism for anchoring said pin or said pin shaft of said pin in said opening in a detachable manner; and a retainer disposed on said clamping surface, said retainer attaching the working disk for preventing the working disk from rotating;

said pin having a further clamping surface for engaging the working disk;

said clamping surface of said shaft or said further clamping surface of said pin being formed by at least one element made from a permanently elastic material;

said mechanism selected from the group consisting of a latching mechanism for detachably anchoring of said pin or said pin shaft and a bayonet lock;

the mandrel having a longitudinal axis and said opening formed parallel to said longitudinal axis;

said end of said shaft being a headpiece;

said latching mechanism including at least one elastic latching element produced from a same material as said shaft or said headpiece;

said pin shaft having at least one recess formed therein for engaging said elastic latching element; and said elastic latching element being one of at least two elastic latching elements fitted at an offset around said longitudinal axis of the mandrel, and said recess on said pin shaft forming a counter-latching element assigned to each of said elastic latching elements.

6. The mandrel according to claim 5, wherein on a circumference of said pin shaft, in a direction of said circumference, said recess is formed and alternates with at least one area of said circumference of said pin shaft where said pin shaft does not have said recess and thus forms said counter-latching element.

7. The mandrel according to claim 1, wherein said pin has an axis, and in relation to said axis of said pin, said groove is formed as a partial length of a spiral or helicoidal line which encompasses said axis of said pin.

8. The mandrel according to claim 3, wherein said clamping surface is formed on said headpiece.

9. The mandrel according to claim 1, further comprising at least one ring fixed on one of said detachable fixing element and said shaft, said ring having an elastic working surface formed from a permanently elastic material.

10. The mandrel according to claim 9, wherein said ring is an O-ring.

11. The mandrel according to claim 3, wherein said opening is formed along said longitudinal axis.

12. The mandrel according to claim 1, wherein the working disk is selected from the group consisting of cut-off disks, grinding disks, and polishing disks.

* * * * *